US008532737B2

(12) United States Patent
Cervantes

(10) Patent No.: US 8,532,737 B2
(45) Date of Patent: Sep. 10, 2013

(54) REAL-TIME VIDEO BASED AUTOMATED MOBILE SLEEP MONITORING USING STATE INFERENCE

(76) Inventor: Miguel Angel Cervantes, Barcelona (ES)

( * ) Notice: Subject to any disclaimer, the term of this patent is extended or adjusted under 35 U.S.C. 154(b) by 1642 days.

(21) Appl. No.: 11/321,840

(22) Filed: Dec. 29, 2005

(65) Prior Publication Data

US 2007/0156060 A1    Jul. 5, 2007

(51) Int. Cl.
*A61B 5/05* (2006.01)
(52) U.S. Cl.
USPC ........... 600/407; 600/307; 600/326; 600/330; 600/476; 600/513
(58) Field of Classification Search
USPC ................. 600/300–307, 326–330, 407, 476, 600/513, 595; 607/42, 59
See application file for complete search history.

(56) References Cited

U.S. PATENT DOCUMENTS

| 5,671,733 A | * | 9/1997 | Raviv et al. | 600/301 |
| 6,070,098 A | * | 5/2000 | Moore-Ede et al. | 600/544 |
| 6,147,612 A | * | 11/2000 | Ruan et al. | 340/575 |

OTHER PUBLICATIONS

Nakajima, K., Matsumoto, Y. and Tamura, T., Development of real-time image sequence analysis for evaluating posture change and respiratory, Physiol. Meas. 22 (2001), N21-N28.

* cited by examiner

*Primary Examiner* — Tse Chen
*Assistant Examiner* — Mark Remaly
(74) *Attorney, Agent, or Firm* — Soquel Group LLC

(57) ABSTRACT

Apparatus for automatically monitoring sleep, including a video recorder for recording live images of a subject sleeping, including a transmitter for transmitting the recorded images in real-time to a mobile device, and a computing device communicating with said transmitter, including a receiver for receiving the transmitted images in real-time, a processor for analyzing in real-time the received images and for automatically inferring in real-time information about the state of the subject, and a monitor for displaying in real-time the information inferred by said processor about the state of the subject. A method and a computer-readable storage medium are also described and claimed.

59 Claims, 12 Drawing Sheets

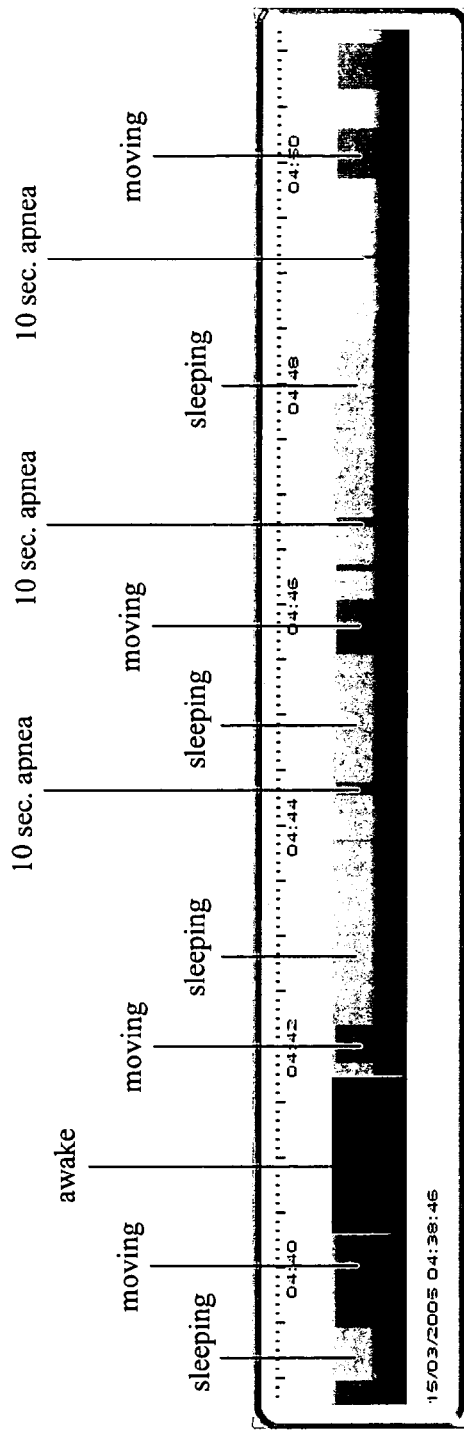
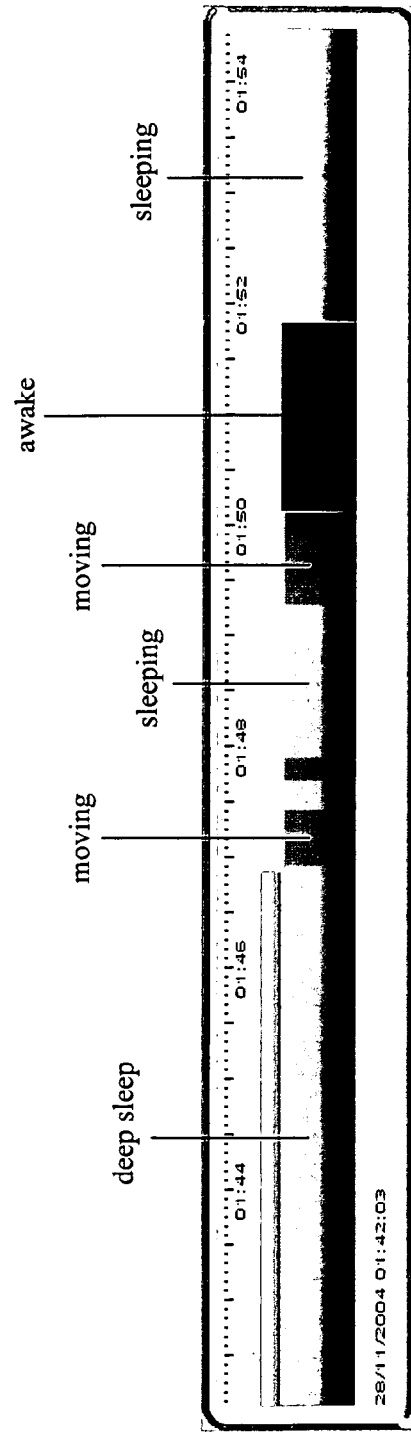
FIG. 10A
FIG. 10B

REAL-TIME VIDEO BASED AUTOMATED MOBILE SLEEP MONITORING USING STATE INFERENCE

FIELD OF THE INVENTION

The present invention relates to digital video processing and automated sleep monitoring.

BACKGROUND OF THE INVENTION

Conventional infant monitors include audio and video monitors that enable parents to continuously hear and see their infant while they are in a different location than the infant. Such devices require continuous manual attention in order to properly alert that parents that something significant is happening; for example, hearing the infant cry or seeing the infant stand up. Such monitors include:
SCBSC769 Baby Monitor, manufactured by Koninklijke Philips Electronics N.V. of Eindhoven, the Netherlands;
Ultimate Range Monitor, manufactured by Fisher-Price, a wholly owned subsidiary of Mattel, Inc., of East Aurora, N.Y.;
YV872 Baby Video Monitor, manufactured by Bébé-Sounds®, a division of Unisar, Inc. of New York, N.Y.;
Baby Quiet Sounds Color Video Monitor, manufactured by Summer Infant, Inc. of Lincoln, R.I.;
GX5200 Color Video Monitoring System, manufactured by SVAT Electronics, Inc.; and
In Sight Baby Video Monitor, manufactured by Safety $1^{st}$, Inc., a division of Dorel Industries, Inc. of Canton, Mass.

Devices such as these that require continuous manual attention have limited use during the night when the parents are sleeping, or during time periods when the parents' focus is distracted.

Advanced infant monitors use sensor pads under the mattress to detect motion, and are able to alert the parents with a "no-movement" alarm. Such monitors include:
Baby Movement Sensor with Sound Monitor, manufactured by BébéSounds®, a division of Unisar, Inc. of New York, N.Y.;
AngelCare®, a movement and sound monitor manufactured by AngelCare Monitors, Inc. of Montreal, Canada; and
BabySense™, an infant respiratory monitor manufactured by Hisense, Ltd. of Rishon LeZion, Israel.

Although devices with sensor pads are able to detect a potential lack of breathing stage, they are not able to identify other stages, such as "infant is standing up" and "infant is turning over".

SUMMARY OF THE DESCRIPTION

The present invention concerns apparatus and methods for automated real-time continuous monitoring of subjects, using image processing to continuously infer information about the states of the subjects. The apparatus of the present invention preferably includes two units, a live video recorder mounted near the subject being monitored and a mobile display unit that is generally remote from the video recorder.

The present invention uses state inference to selectively activate a display monitor and sound an alert, so that continuous monitoring is not required but is optionally enabled at will. The present invention does not rely on sensor pads under the mattress, and does not impose physical constraints on the subject being monitored. Using motion detection and state inference, the present invention is able to distinguish between a variety of states such as "standing up", "lying on stomach", "lying on back", "occasionally turning over", "crying", "thrashing", "vomiting" and "out of view".

The present invention is particularly advantageous for parents who wish to monitor their infants from their bedrooms during the night. Instead of continuously playing recorded sound while the parents are sleeping, the apparatus of the present invention may be set to continuously monitor the infant in real-time, but to selectively activate a display and a speaker when a state of alert occurs. A state of alert occurs when a state of the infant is detected that is deemed to be significant.

The present invention is also advantageous for parents who are monitoring their infants during the day, while the parents are awake. The apparatus of the present invention may be set to continuously display an indication of the state of the infant, which provides an instant diagnosis to the parents, and to sound an alarm when a state of alert is encountered. Optionally, the apparatus may also be set to continually display images of the infant and to continuously play recorded sound, so that the parents can instantly examine the monitored images and sound in more detail at any time.

It may be appreciated that by including automatic state inference, the present invention provides an additional safety precaution over conventional baby monitors. In case the audio or video fails, or is accidentally switched off, or too low to hear on the receiver, a state alert, such as "baby is crying", can nevertheless make the parents aware of an alarm.

The present invention has direct application to sleep apnea monitoring, where a subject is being self-monitored or monitored by others. Apparatus of the present invention continuously records images of a subject, while the subject is sleeping, and processes the recorded images to infer states of the subject. Important sleep states that can be inferred by the present invention include "obstructive apnea with durations between 10 sec. and 20 sec.", "obstructive apnea with duration longer than 20 sec.", "central apnea with duration between 10 sec. and 20 sec.", "central apnea with duration longer than 20 sec.", "abnormal movement", "low rhythm of breathing" and "deep sleep". An alarm is sounded when a state of alert is inferred.

Additionally, a time history of state information and images is stored for post-analysis review and diagnosis. Such post-analysis can provide the subject with a statistical analysis of his sleep patterns and interferences. Conventional apnea monitors require a subject to wear an oxygen mask while sleeping, in order to measure intake and outtake airflows; or a belt that is worn around the chest, which can be uncomfortable. In distinction, the present invention uses a video recorder, which is not in direct contact with the subject being monitored.

A first preferred embodiment of the present invention uses an architecture wherein the mobile display device performs the image processing and state detection, and the video recorder can be a simple inexpensive recording device. A second preferred embodiment of the present invention uses an architecture wherein the video recorder performs the image processing and state detection, and the mobile display unit can be a simple and inexpensive display device.

Use of video images to analyze posture changes and respiration rates of subjects is described in Nakajima, K., Matsumoto, Y. and Tamura, T., "Development of real-time image sequence analysis for evaluating posture change and respiratory rate of a subject in bed", *Physiol. Meas.* 22 (2001), pgs. N21-N28. Nakajima et al. describe generating a waveform from captured video images, that approximates true respiratory behavior. Nakajima et al. use optical flow measurements to estimate motion velocities. They describe real-time generation of waveforms of average velocities. They also relate visual patterns within average velocity waveforms to states including "respiration", "cessation of breath", "full posture change", "limb movement", and "out of view".

Although Nakajima et al. identify states manually from visual inspection of their waveforms, they do not disclose automated inference of states. That is, they do not describe an automated way of detecting states from their waveform. In distinction, the present invention automatically infers states in real-time, and includes a continuous display of state information. Thus, using the present invention, the person monitoring the subject can be a layperson without the know-how to analyze optical flow waveforms.

There is thus provided in accordance with a preferred embodiment of the present invention apparatus for automatically monitoring sleep, including a video recorder for recording live images of a subject sleeping, including a transmitter for transmitting the recorded images in real-time to a mobile device, and a computing device communicating with the transmitter, including a receiver for receiving the transmitted images in real-time, a processor for analyzing in real-time the received images and for automatically inferring in real-time information about the state of the subject, and a monitor for displaying in real-time the information inferred by the processor about the state of the subject.

There is further provided in accordance with a preferred embodiment of the present invention a method for automated sleep monitoring, including recording live images of a subject sleeping, transmitting the recorded images in real-time to a computing device, receiving the transmitted images in real-time at the computing device, analyzing the received images at the computing device in real-time, automatically inferring information about the state of the subject at the computing device in real-time, and displaying the information inferred about the state of the subject in real-time on a monitor coupled with the computing device.

There is yet further provided in accordance with a preferred embodiment of the present invention apparatus for automatically monitoring sleep, including a video recorder for capturing live images of a subject sleeping, including a processor for analyzing in real-time the captured images and for automatically inferring in real-time information about the state of the subject, and a transmitter for transmitting the information inferred by the processor about the state of the subject in real-time to a mobile device, and a display device communicating with the transmitter, including a receiver for receiving the transmitted information inferred by the processor about the state of the subject, and a monitor for displaying in real-time the received information inferred by the processor about the state of the subject.

There is moreover provided in accordance with a preferred embodiment of the present invention a method for automated sleep monitoring, including capturing live images of a subject sleeping, analyzing the captured images in real-time, automatically inferring information about the state of the subject in real-time, transmitting the information inferred about the state of the subject to a display device, receiving the transmitted information inferred about the state of the subject in real-time at the display device, and displaying the received information inferred about the state of the subject in real-time on the display device.

There is additionally provided in accordance with a preferred embodiment of the present invention a computing device for automatically monitoring sleep, including a receiver for receiving images of a subject sleeping from a live video recorder, a processor for analyzing in real-time the received images and for automatically inferring in real-time information about the state of the subject, and a monitor for displaying in real-time the information inferred by the processor about the state of the subject.

There is further provided in accordance with a preferred embodiment of the present invention a method for automated sleep monitoring, including receiving live images of a subject sleeping from a video recorder, analyzing the received images in real-time, automatically inferring information about the state of the subject in real-time, and displaying the information inferred about the state of the subject in real-time on a monitor.

There is yet further provided in accordance with a preferred embodiment of the present invention an enhanced video recorder for automatically monitoring sleep, including a memory for storing captured digital images of a subject sleeping, a processor for analyzing in real-time the captured images and for automatically inferring in real-time information about the state of the subject, and a transmitter for transmitting the information inferred by the processor about the state of the subject in real-time to a display device.

There is moreover provided in accordance with a preferred embodiment of the present invention a method for automated sleep monitoring, including capturing images of a subject sleeping, analyzing the capturing images in real-time, automatically inferring information about the state of the subject in real-time, and transmitting the information inferred about the state of the subject to a display device in real-time.

There is additionally provided in accordance with a preferred embodiment of the present invention a computer-readable storage medium storing program code for causing a computing device to receive transmitted live images of a subject sleeping in real-time, analyze the received images in real-time, automatically infer information about the state of the subject in real-time, and display the information inferred about the state of the subject in real-time on a monitor coupled with the computing device.

There is further provided in accordance with a preferred embodiment of the present invention a computer-readable storage medium storing program code for causing a video recorder to capture images of a subject sleeping, analyze the capturing images in real-time, automatically infer information about the state of the subject in real-time, and transmit the information inferred about the state of the subject to a display device.

BRIEF DESCRIPTION OF THE DRAWINGS

The present invention will be more fully understood and appreciated from the following detailed description, taken in conjunction with the drawings in which:

FIGS. 10A and 10B are more detailed illustrations of a time-line display of FIG. 9, in accordance with a preferred embodiment of the present invention;

DETAILED DESCRIPTION

Figure 1:
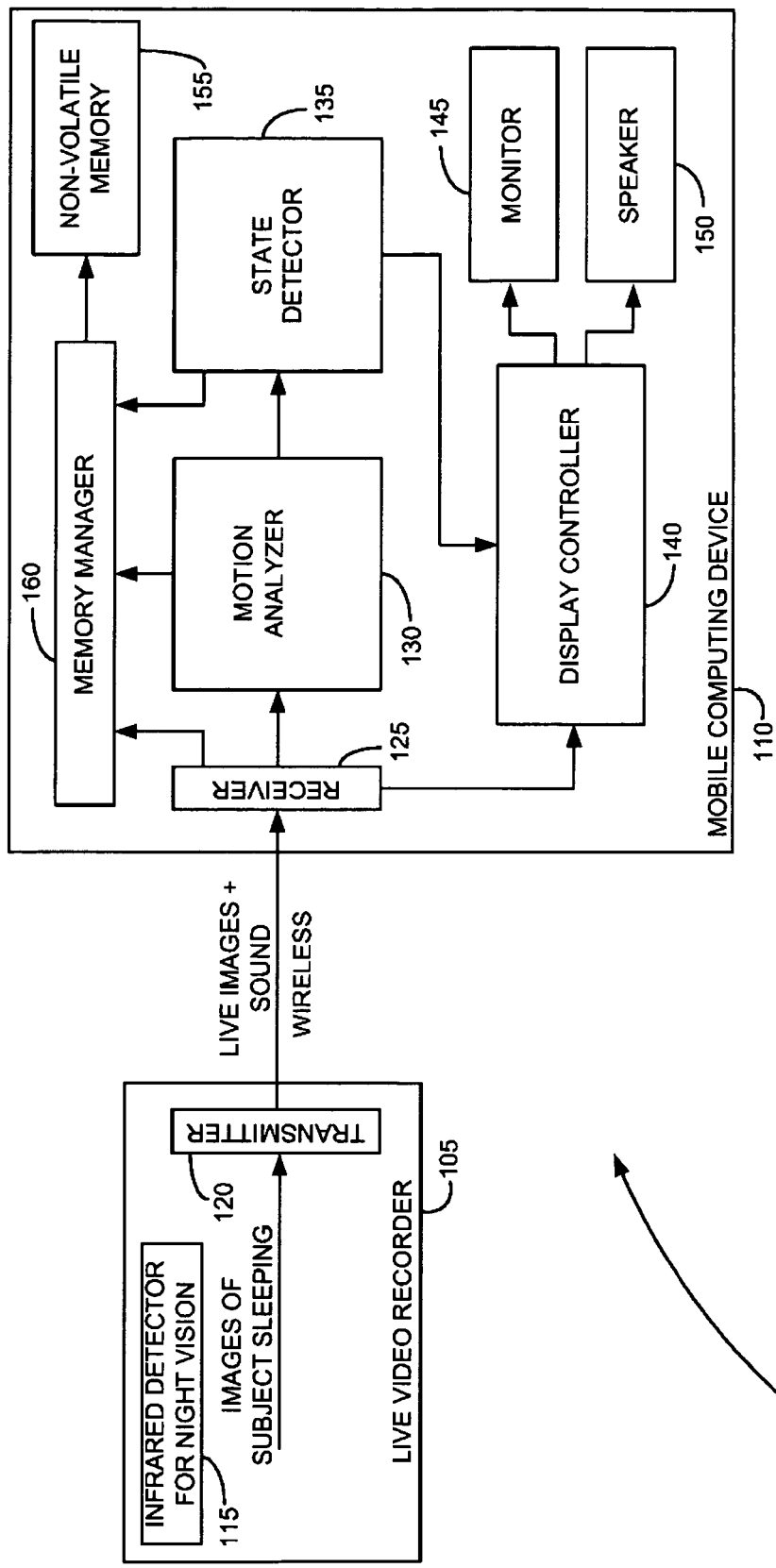
FIG. 1 is a simplified block diagram of a real-time mobile sleep monitoring system according to a first embedded architecture, wherein state analysis is performed by a mobile computing device, in accordance with a preferred embodiment of the present invention.

The present invention concerns an apparatus and method for automated real-time sleep monitoring, based on analysis of live recorded video of a subject sleeping. The present invention has application to devices that enable parents to monitor their infants, and to devices that enable physicians to monitor patients for sleep disorders such as apnea. The present application also has application to self-monitoring, for subjects who wish to monitor their own sleep behavior and be alerted when various states of alert are inferred, and be able to post-diagnose their sleep behavior with statistical analysis. Similar in spirit to devices that enable people to monitor their pulse as a general health indicator, devices of the present invention enable people to monitor their sleep as a healthy sleep indicator.

Overall, in a preferred embodiment, the present invention includes two units; namely, a live video recorder that is mounted in the vicinity of the subject being monitored, and a mobile monitoring unit that is located where the monitoring is taking place. Generally, these two units are remote from one another, and the video recorder preferably communicates with the monitoring unit via wireless communication. However, in self-monitoring applications, where a subject is monitoring his own sleep, the units can be combined functionally into a single unit.

The present invention performs real-time high-sensitivity motion detection on the images that are recorded by the video recorder, as described hereinbelow, and automatically infers state information about the subject being monitored, without manual intervention. Whereas prior art infant monitors require constant remote manual attention to the images and sound in order to identify states of the subject, the present invention uses state detection to automate this process, as described hereinbelow. As such, the present invention is able to automatically detect states such as "infant is sleeping", "infant is standing up", "infant is lying on stomach", "infant is lying on back", "infant is occasionally turning over", "infant is crying", "infant is thrashing" and "infant is vomiting".

It may be appreciated that by performing automatic state inference, the present invention provides an additional safety measure over conventional baby monitors. In case the audio or video monitoring fails, or is accidentally switched off, or is too low to hear on the receiver, an automatic state alert, such as "baby is crying", can nevertheless make the parents aware of an alarm.

Automated motion detection of the present invention is able to precisely filter out noise, and thereby accurately estimate even subtle motions of a subject. As such, the present invention applies even in situations where the subject is covered with layers of sheets and blankets.

Automated state inference of the present invention relies on several indicators. One such indicator is repetitiveness of detected movements. Empirical studies have shown that a repetitiveness pattern of a subject's movements while the subject is sleeping is very different than a repetitiveness pattern of a subject's movements while the subject is awake. Similarly, a repetitiveness pattern of movement is different for soft sleep than it is for deep sleep.

In accordance with a preferred embodiment of the present invention, repetitiveness is used as a characteristic of a subject's sleep. For example, when a subject moves, his repetitiveness pattern is broken for a short amount of time. Similarly, regarding the various stages of sleep, during the rapid eye movement (REM) stage and the stage preceding REM sleep, a subject is generally in a semi-paralyzed state where his body is paralyzed with the exception of vital muscles involved in the breathing process. Such features of sleep, combined with analysis of the subject's movements during sleep, enable the present invention to determine a likelihood that the subject is in a given stage at any given time. Thus if the subject is moving, which is manifested in a lack of repetitiveness, then he is more likely to be in a soft sleep; whereas if the subject does not move for a specific amount of time, which is manifested in a presence of repetitiveness, then he is more likely to be in a deep sleep. A general summary of the various stages of sleep is available at http://www.sleepdisorderchannel.net/stages/.

Apparatus of the present invention preferably also maintains a time history log of state information and images, for post-analysis study and diagnosis. For example, a subject using the present invention to self-monitor his sleep may use such a time history of state data, such as the percentage of time a subject's total sleep is in deep sleep over a specified time period such as one week or one month, for deriving statistical measures of the quality of his sleep.

For patents monitoring their infant, the time history log preferably includes inter alia (i) a summary of the infant's last night's sleep, including times when the infant awoke or otherwise changed states; (ii) average of the infant's last week's or last month's sleep statistics, or such other time period; and (iii) a comparison of the infant's last night's sleep to that of the last week or month, or such other time period. Preferably, a user of the present invention presses one or more buttons to enable a display of such log information.

The present invention has two general embodiments; namely, a first embodiment (FIGS. 1, 2 and 4 below) in which the image processing required to infer state information is performed at the remote monitoring unit, and a second embodiment (FIGS. 3 and 5 below) in which the image processing is performed at the recording unit. In addition, the first embodiment has an embedded implementation (FIG. 1 below) and a non-embedded implementation (FIG. 2 below). Each embodiment has advantages over the other relating to hardware complexity, cost and interoperability.

Figure 2:
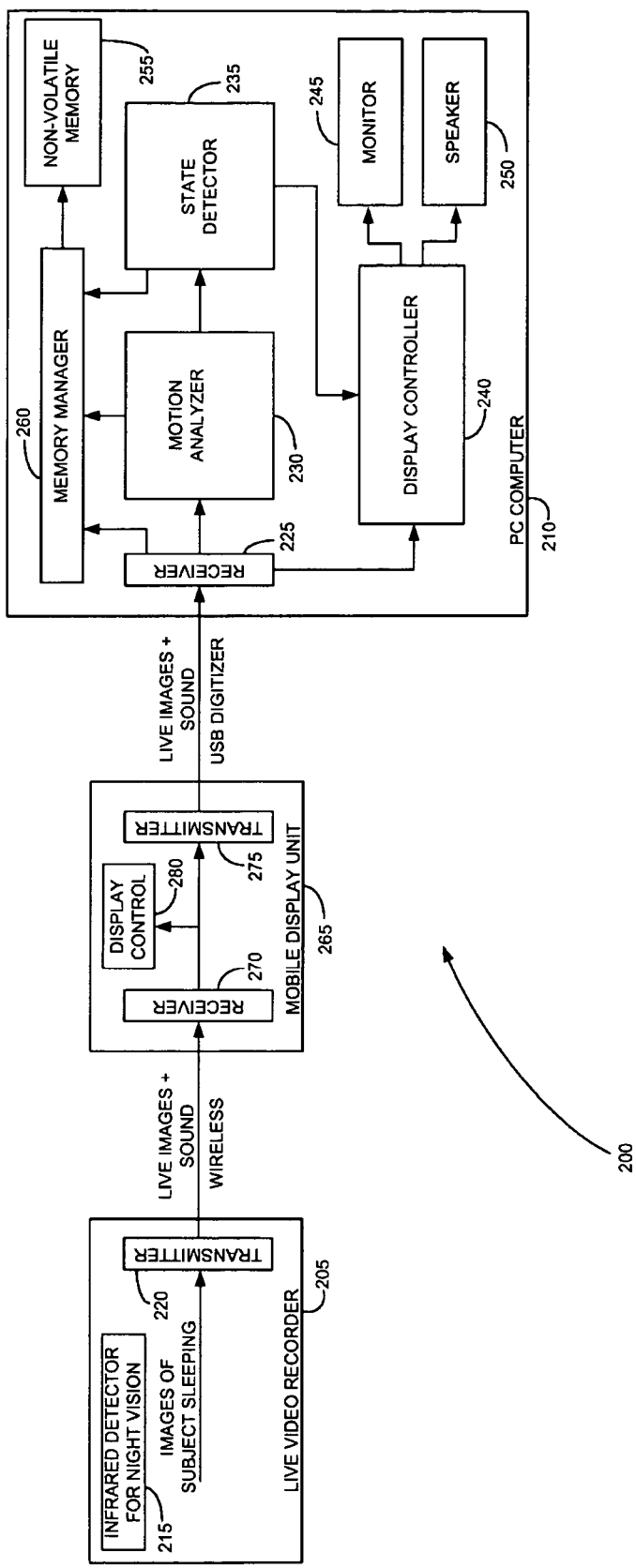
FIG. 2 is a simplified block diagram of a non-embedded version of the monitoring system of FIG. 1 whereby the mobile computing device is a PC computer that is connected to a remote display unit, in accordance with a preferred embodiment of the present invention.

Reference is now made to FIG. 1, which is a simplified block diagram of a real-time mobile sleep monitoring system according to a first embedded architecture, wherein state analysis is performed by a mobile computing device, in accordance with a preferred embodiment of the present invention. Shown in FIG. 1 is an overall system including a live video recorder 105, which records images of a subject while the subject is sleeping, and a mobile computing device 110, which processes the recorded images and infers real-time information about the state of the subject. Preferably, video recorder 105 is mounted on a wall or on a bed or on another piece of furniture in the vicinity of the subject, in such a way that video recorder 105 can capture accurate images of the subject while he is sleeping. For example, if the subject is an infant who is sleeping in a crib, then video recorder 105 may be mounted on the crib or on the wall above the crib, and directed at the sleeping infant.

Preferably, a particular feature of video recorder 105 is the ability to take clear images in a dark surrounding, since this is the typical surrounding in which subjects sleep. To this end, video recorder 105 preferably includes an infrared detector 115 or such other heat sensitive or light sensitive component used to enhance night vision.

In accordance with a preferred embodiment of the present invention, mobile computing device 110 is used to monitor the subject at a site that is remote from the location of video recorder 105. For example, if the subject is an infant who is sleeping in a crib as above, then mobile computing device 110 may be located in the parents' bedroom, so that the parents can monitor their infant at night.

Video recorder 105 includes a transmitter 120, which transmits the recorded images in real-time to a receiver 125 within mobile computing device 110. Preferably transmitter 120 transmits the recorded images using wireless communication, so that no physical wires are required to connect video recorder 105 with mobile computing device 110.

As receiver 125 receives the transmitted images, the images are passed to a motion analyzer 130, which performs high sensitivity motion detection as described in detail hereinbelow. The results of motion analyzer 130 are passed to a state detector 135, which infers a state of the subject, as described in detail hereinbelow. For monitoring infants, states may include inter alia "sleeping", "awake", "standing up", "lying on back", "lying on stomach", "moving", "occasionally turning over", "crying", "thrashing" and "vomiting". For monitoring sleep apnea, states may include inter alia "obstructive apnea with duration between 10 sec. and 20 sec.", "obstructive apnea with duration longer than 20 sec.", "central apnea with duration between 10 sec. and 20 sec.", "central apnea with duration longer than 20 sec.", "abnormal movement", "low rhythm of breathing" and "deep sleep".

State information inferred by state detector 135 is passed to a display controller 140. As shown in FIG. 1, display controller 140 controls both a monitor 145 and a speaker 150. It may be appreciated by those skilled in the art that display controller 140 may include two separate device controllers, a first device controller for displaying data on monitor 145 and a second device controller for playing sound on speaker 150. Display controller 140 is used for displaying state information on monitor 145.

Optionally, display controller may also be used for displaying the recorded images received by receiver 125 on monitor 145. If video recorder 105 also records sound, then the recorded sound may also be transmitted from transmitter 120 to receiver 125, and display controller 140 may also be used for playing the sound on speaker 150. The capability for mobile computing device 110 to display the recorded images and to play the recorded sound may be excluded from the hardware, or alternatively may be enabled in the hardware and selectively activated by a user of mobile computing device 110.

For example, if parents are monitoring their sleeping infant in their bedroom, they may prefer that the images and sound not be continuously played, as the light from monitor 145 and the sound from speaker 150 may disturb their sleep. Instead, they may prefer that display controller 140 selectively activate monitor 145 or speaker 150 only when state detector 135 infers a state that is deemed to be significant, such as "infant is awake", "infant is moving" or "infant is crying". When such a state if detected, monitor 145 may be activated to automatically display a message describing the state of the subject, and to display the current images being recorded, and speaker 150 may be activated to automatically sound an alert and to play the current sound being recorded.

Alternatively, if parents are monitoring their sleeping infant in their dining room while having dinner, they may instead prefer that display controller 140 continuously display the recorded images on monitor 145 and play the recorded sound on speaker 150. Such displays provide instant and constant availability of information.

It may be appreciated that there are various display options each of which may be suitable for a particular scenario, such as any combination of: (i) continuous or selective display of video, (ii) continuous or selective sound play, and (iii) continuous or selective state display. Selective display preferably occurs when an alert state is inferred, where an alert state is a state deemed to be significant. Specifically, the apparatus of the present invention may use settings for various modes, as described in Table I.

TABLE I

Monitoring Settings

| Mode | Setting |
| --- | --- |
| Daytime monitoring mode, for parents monitoring infants | Continuous display of state information; continuous display of images; continuous sound play; sound of alarm when a state of alert is inferred |
| Nighttime monitoring mode, for parents monitoring infants | Selective display of state information and sound of alarm when a state of alert is inferred; selective display of images; selective sound play |
| Self-monitoring mode, for adults monitoring themselves for sleep apnea | Selective display of state information when a state of alert is inferred; log history of images and states for post-analysis diagnosis |

It will be appreciated by those skilled in the art that different combinations of settings than those listed in Table I may be used instead for the various modes.

From a hardware perspective, if mobile computing device 110 is limited to only displaying state information and sounding beeper alerts, and is not enabled to display continuously recorded images and play continuously recorded sound, then the hardware can be manufactured at a much lower cost.

Also shown in FIG. 1 is a non-volatile memory 155 which is managed by a memory manager 160. Memory manager 160 can be used for logging in memory 155 a time history of images and information that describes the subject's sleep. Such a history can be used for post-analysis, including statistical analysis of sleep patterns and interference.

The architecture of FIG. 1 delegates the work of motion analysis and state detection to mobile computing device 110. An advantage of this architecture is that a conventional off-the-shelf video recorder that has wireless transmission capability can be used for video recorder 105. Thus mobile computing device 110 is interoperable with a wide variety of video recorders.

Reference is now made to FIG. 2, which is a simplified block diagram of a real-time mobile sleep monitoring system according to a non-embedded version of the architecture of FIG. 1 that uses a conventional mobile display unit 265 connected with a PC computer 210, as a substitute for mobile computing device 110, in accordance with a preferred embodiment of the present invention. Shown in FIG. 2 are the components of FIG. 1, together with mobile display unit 265 that includes a receiver 270 for receiving images and sound from video recorder 205 over a wireless communication, and a transmitter 275 for transmitting the images and sound to PC computer 210. Preferably, mobile display unit 265 is connected to PC computer 210 via a USB digitizer or an IEEE 1394 connection, or such other standard digital transmission connection, which continuously communicates digitized display frame data from mobile display unit 265 to PC computer 210. Optionally, mobile display unit 265 may have its own display control 280 for viewing images directly on mobile display unit 265.

Preferably, PC computer 210 runs a software application that processes the incoming images from mobile display unit 265 and performs the state inference; i.e., that performs the operations of motion analyzer 230 and state detector 235. With this architecture, the present invention can be implemented using a conventional baby monitor that comes with a video recorder and a separate display unit.

Figure 8:
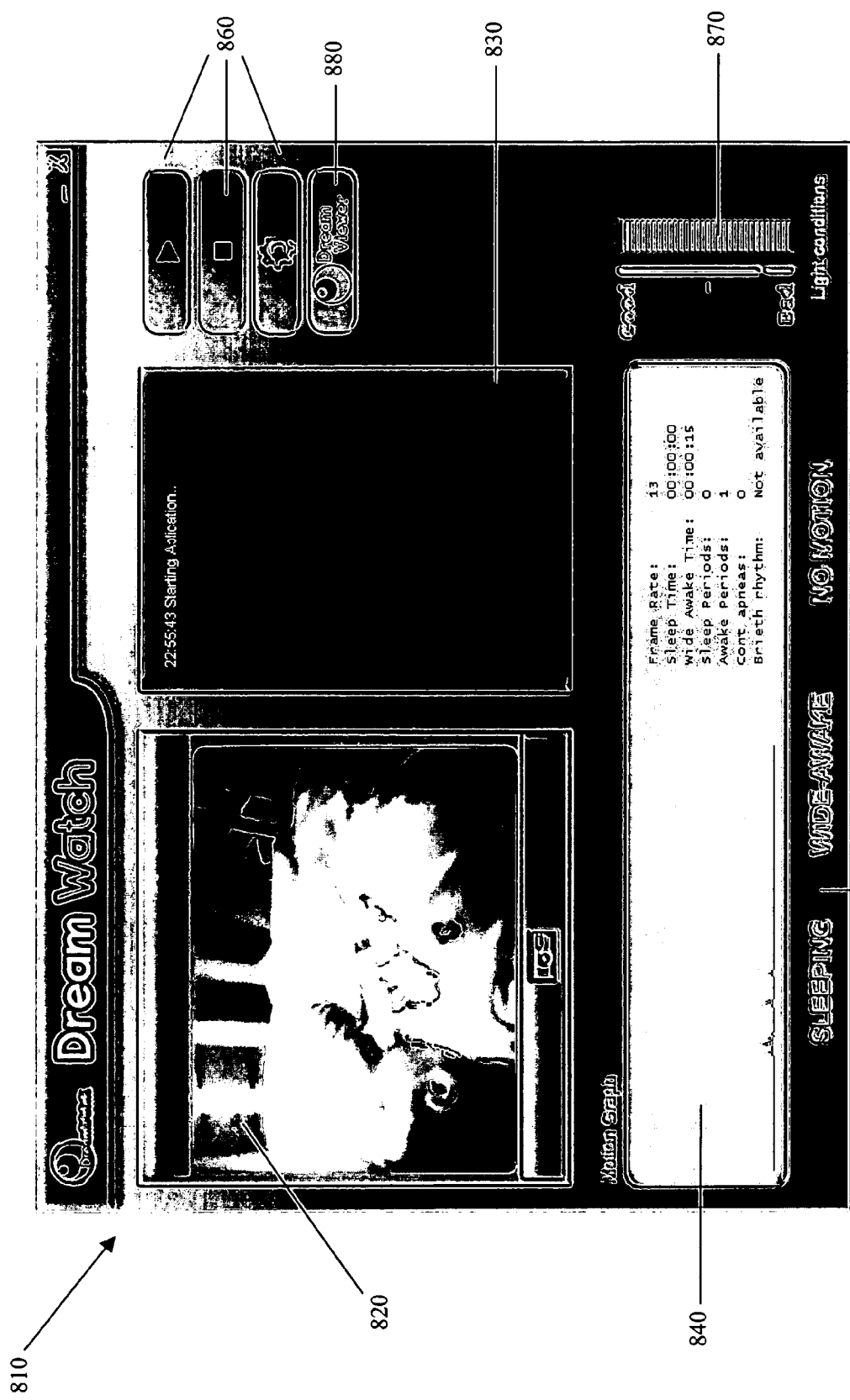
FIG. 8 is an illustration of a user interface window for real-time automated sleep monitoring, in accordance with a preferred embodiment of the present invention.
Figure 9:
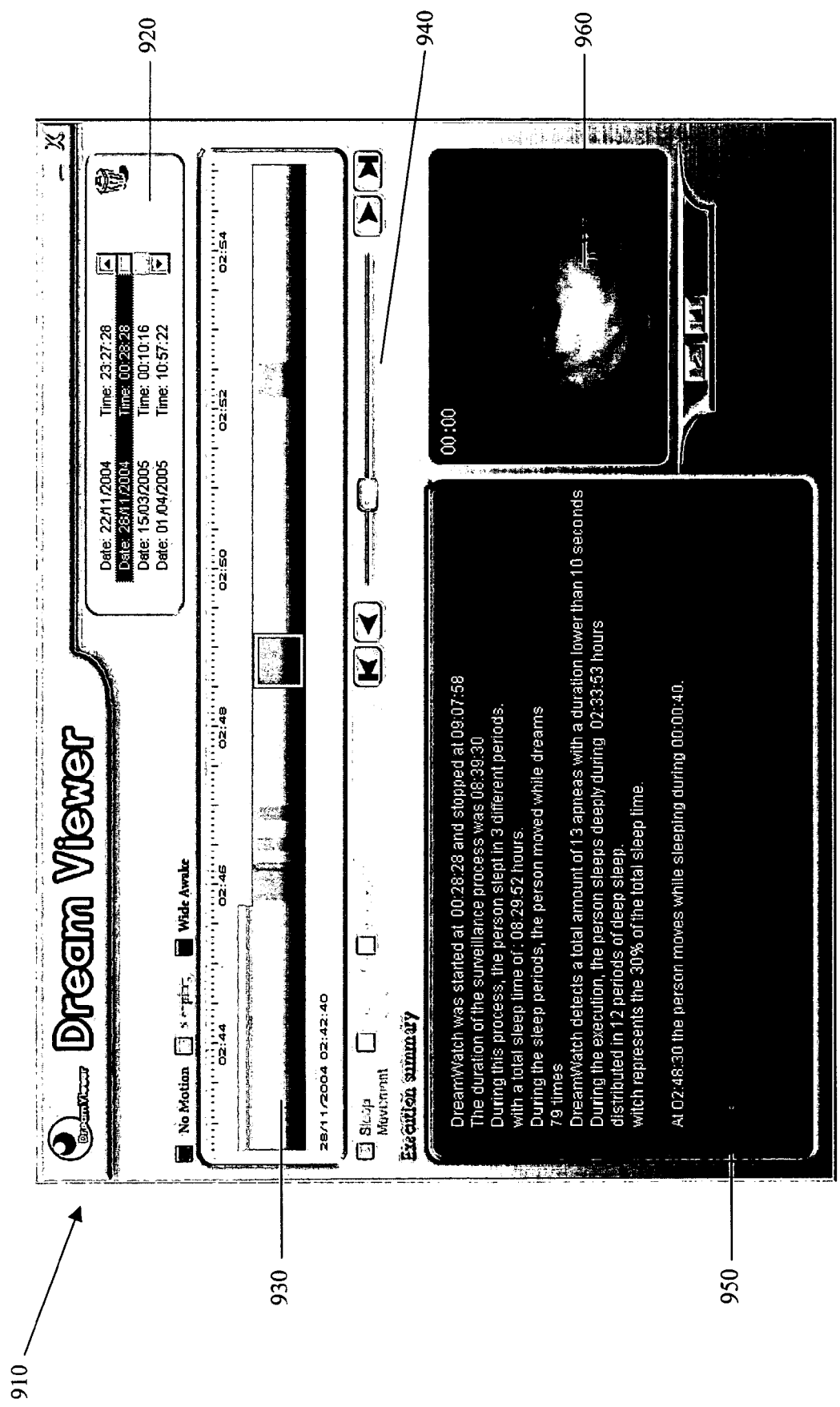
FIG. 9 is an illustration of a user interface window for post-session review of images and state data collected during one of a plurality of sleep monitoring sessions, in accordance with a preferred embodiment of the present invention.
Figure 11:
FIG. 11 is an illustration of a user interface window for monitoring infants, in accordance with a preferred embodiment of the present invention.

Another advantage of using a PC computer running special purpose software is the enhanced user interface that it provides, as illustrated in FIGS. 8, 9 and 11. The PC offers the ability to design a detailed user interface that responds to full keyboard and mouse inputs. In distinction, baby monitor display units generally have very limited user interface display and control capabilities. It may be appreciated by those skilled in the art that the system of FIG. 1 is an embedded version of the system of FIG. 2, where the processing performed by PC computer 210 is embedded within the mobile display unit.

Figure 3:
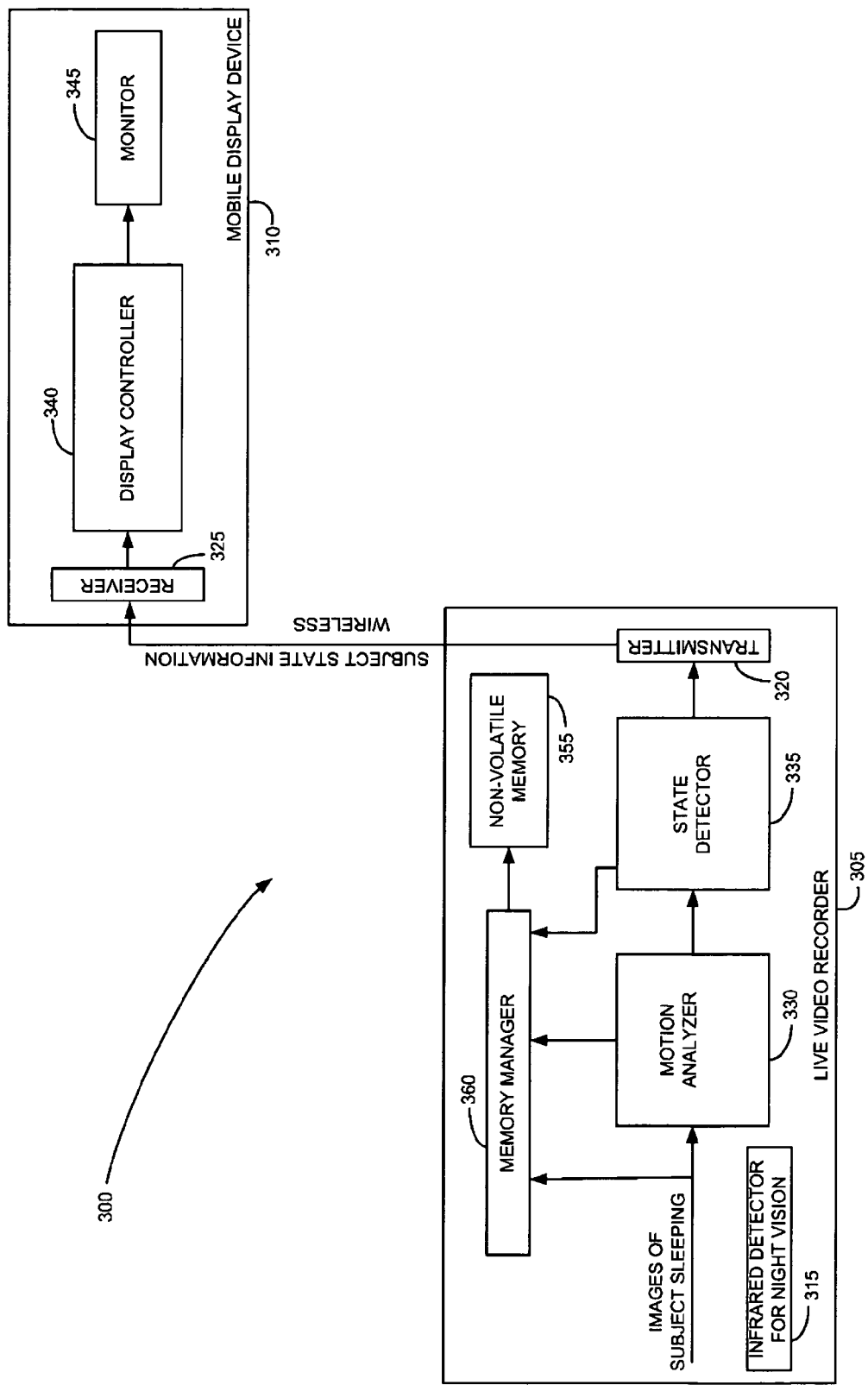
FIG. 3 is a simplified block diagram of a real-time mobile sleep monitoring system according to a second embedded architecture, wherein state analysis is performed by a video capture device, in accordance with a preferred embodiment of the present invention.

Reference is now made to FIG. 3, which is a simplified block diagram of a real-time mobile sleep monitoring system according to a second embedded architecture, wherein state analysis is performed by a video capture device, in accordance with a preferred embodiment of the present invention. Shown in FIG. 3 is an overall system including a live video recorder 305 and a mobile display device 310. Video recorder 305 captures live images of a subject sleeping.

Video recorder 305 is used to capture images of a subject sleeping. Preferably, video recorder has the ability to capture clear images within a dark surrounding, since this is typically the surrounding in which subjects sleep. To this end, video recorder 305 preferably includes an infrared detector 315, or such other heat sensitive or light sensitive detector.

Video recorder 305 includes a motion analyzer 330, which processes the recorded images to derive high-sensitivity motion detection. Results of motion analyzer 330 are passed to a state detector 335, which infers information about the state of the sleeping subject.

State information inferred by state detector 335 is passed to a transmitter 320 within video recorder 305, which transmits the state information to a receiver 325 within mobile display device 310. Preferably, transmitter 320 uses wireless communication so that video recorder need not be connected to mobile display device with physical wires.

Receiver 325 passes the received state information to a display controller 340, which controls a monitor 345. Display controller 340 activates monitor 345 to display state information, for viewing by a person remotely monitoring the sleeping subject.

Display controller 340 may continuously activate monitor 345, or may activate monitor 345 only when the state information is deemed to be significant. Display controller 340 may also activate mobile display device 310 to sound an alarm when the state information is deemed to be significant.

Video recorder 305 may optionally include non-volatile memory 355 and a memory manager 360, which logs in memory 355 a time history of images and state data that describes the subject's sleep during the night. Such a time history can be used for post-analysis, to study the subject's sleep pattern and interference.

The architecture in FIG. 3 performs the motion analysis and state detection within video recorder 305. As such, mobile display device 310 can be a simple inexpensive display unit, and the amount of data that flows between transmitter 320 and receiver 325 is minimal and requires only a small amount of bandwidth. It will be appreciated by those skilled in the art that whereas the system of FIG. 1 embeds the image processing within the mobile display unit, the system of FIG. 3, in distinction, embeds the image processing within the video recorder.

Figure 4:
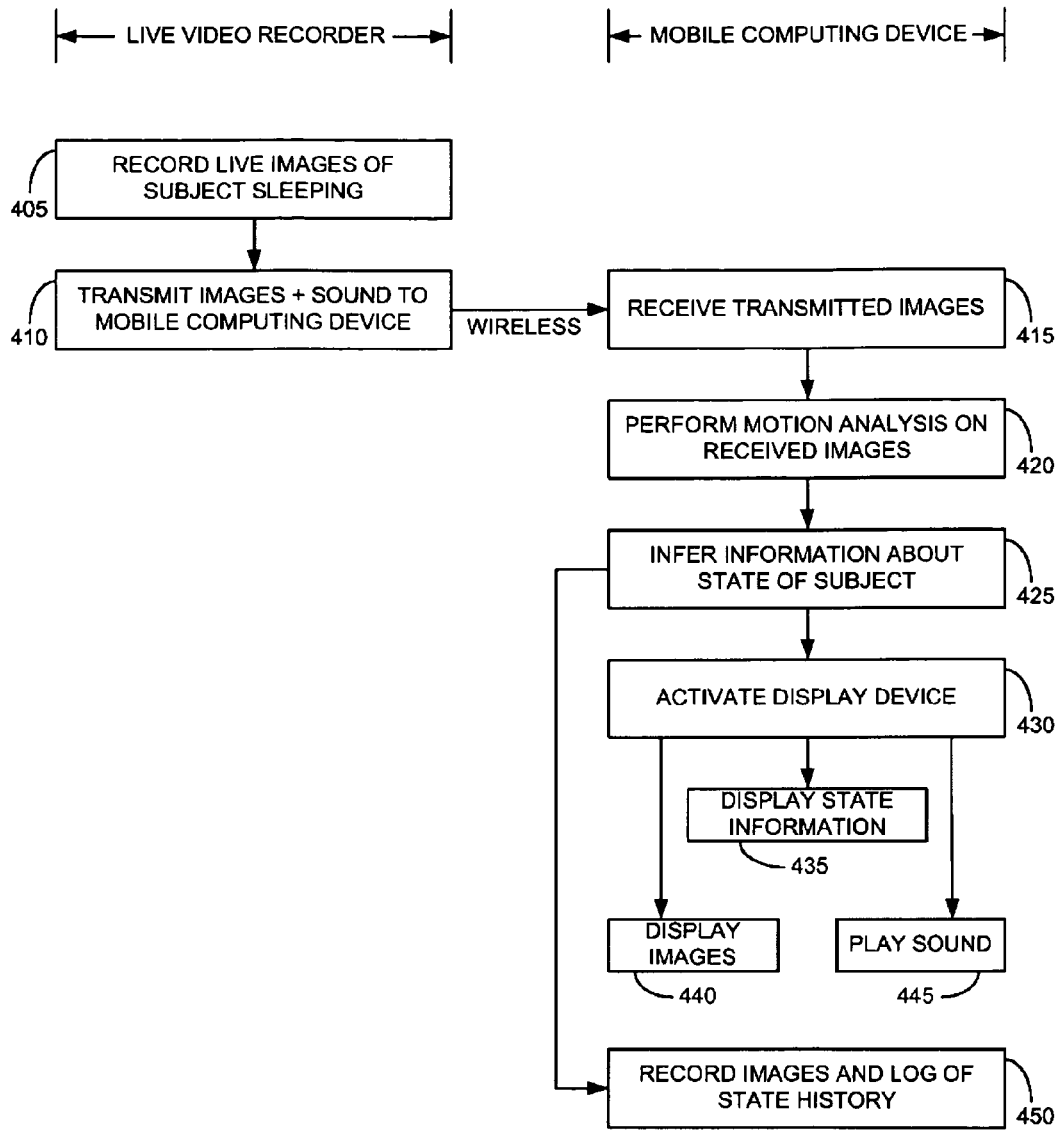
FIG. 4 is a simplified flowchart for a method of monitoring sleep at a mobile device in real-time according to a first architecture, wherein state analysis is performed by the mobile device, in accordance with a preferred embodiment of the present invention.

Reference is now made to FIG. 4, which is a simplified flowchart for a method of monitoring sleep at a mobile device in real-time according to a first architecture, wherein state analysis is performed by the mobile device, in accordance with a preferred embodiment of the present invention. The left column of FIG. 4 indicates steps performed by a live video recorder that records images of a subject sleeping, and the right column of FIG. 4 indicates steps performed by a mobile computing device that monitors the sleeping subject.

At step 405 the video recorder continuously records live images of the subject sleeping. Optionally, the video recorder may also continuously record sound. At step 410 the video recorder transmits the images, and optionally the sound, in real-time to the mobile computing device, preferably via wireless communication. At step 415 the mobile computing device receives the images. At step 420 the mobile computing device analyzes the received images and derives high-sensitivity motion analysis, as described in detail hereinbelow. At step 425 the mobile computing device infers state information about the subject based on results of the motion analysis step. At step 430 the mobile computing device actives a monitor, and optionally also activates a speaker. At step 435 the mobile computing device displays state information about the sleeping subject on a monitor. Optionally, at step 440 the mobile computing device displays the received images on the monitor, and at step 445 the mobile computing device plays recorded sound on the speaker.

In addition to displaying real-time state information at step 435, the mobile computing device may also perform step 450 to maintain a time history log of images and state data related to the subject's sleep. Such a log is preferably used for post-analysis, to derive statistics about the subject's sleep patterns and interference, and to identify and study significant events that occurred during the night.

The architecture in FIG. 4 performs step 420 of motion analysis and step 425 of state inference on the mobile computing device. As such, the mobile computing device is preferably equipped with appropriate hardware to perform image processing.

Figure 5:
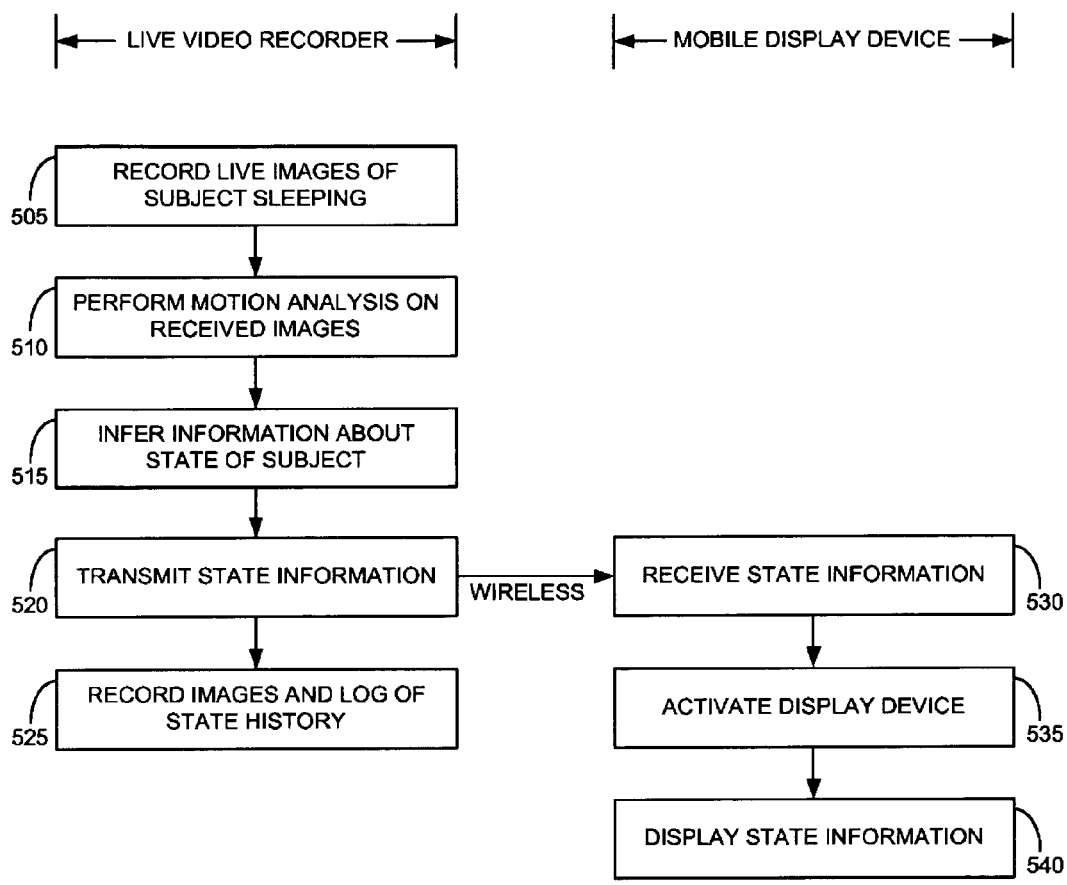
FIG. 5 is a simplified flowchart for a method of monitoring sleep at a mobile device in real-time according to a second architecture, wherein state analysis is performed by a video capture device, in accordance with a preferred embodiment of the present invention.

Reference is now made to FIG. 5, which is a simplified flowchart for a method of monitoring sleep at a mobile device in real-time according to a second architecture, wherein state analysis is performed by a video capture device, in accordance with a preferred embodiment of the present invention. The left column of FIG. 5 indicates steps performed by a live video recorder that captures images of a subject in bed, and the right column of FIG. 5 indicates steps performed by a mobile display unit that is used to monitor the subject.

At step 505 the video recorder captures live images of the subject in bed. At step 510 the video recorder analyzes the captured images in real-time, and derives high-sensitivity motion detection. At step 515 the video recorder infers state information about the sleeping subject, based on the results of motion analysis step 510. At step 520 the video recorder transmits the inferred state information to the mobile display device, preferably via wireless communication.

Optionally, at step 525 the video recorder logs a time history of images and state data relating to the subject's sleep during the night. Such information is preferably used for post-analysis diagnosis, to study the subject's sleep patterns and disturbances.

At step 530 the mobile display device continuously receives the state information that is being transmitted at step 520. At step 535 the mobile display device activates a monitor, and at step 540 the mobile display device displays the state information on the monitor.

The architecture in FIG. 5 performs the motion analysis step 510 and the state inference step 515 at the video recorder, and not at the mobile display device. As such, the mobile display device can be a simple and inexpensive display unit.

Motion Detection

Figure 6:
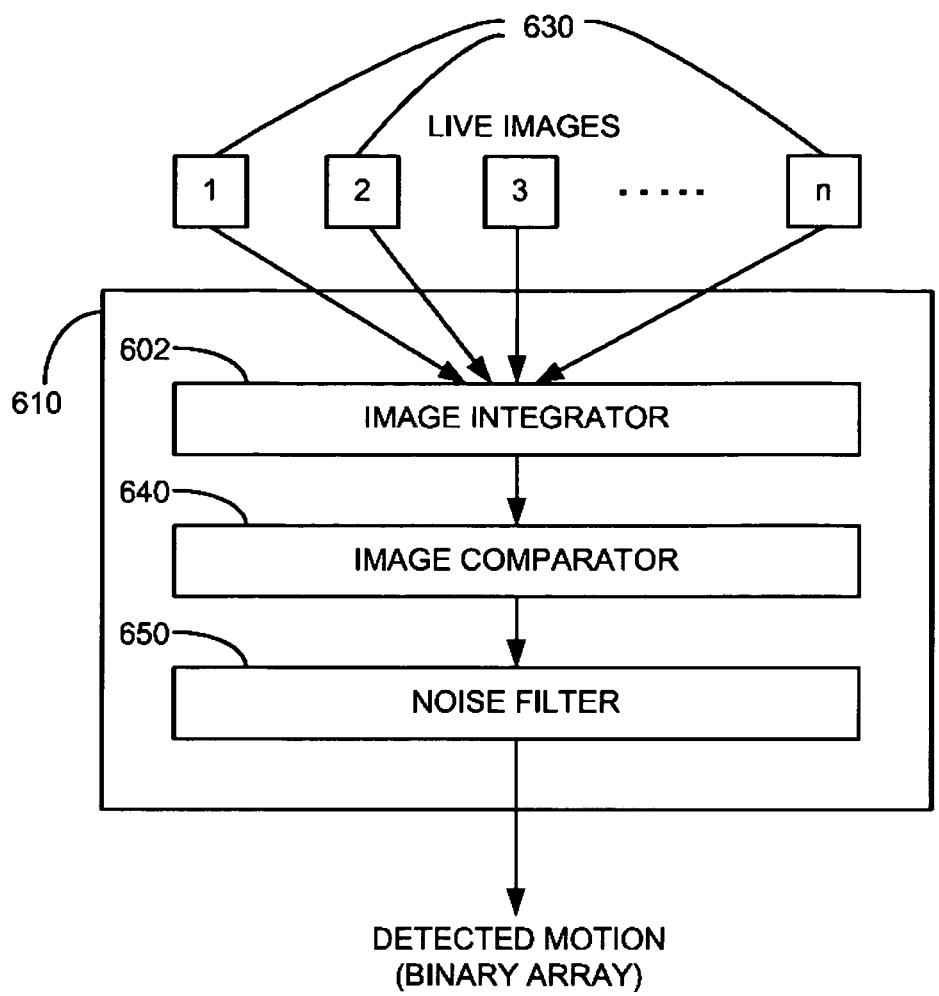
FIG. 6 is a simplified block diagram of a high-sensitivity motion analyzer in accordance with a preferred embodiment of the present invention.

The operation of motion analyzers 130, 230 and 330 in FIGS. 1-3, respectively, and motion analysis steps 420 and 510 in FIGS. 4 and 5, respectively, will now be described in detail. Reference is now made to FIG. 6, which is a simplified block diagram of a high-sensitivity motion analyzer 610, in accordance with a preferred embodiment of the present invention. Motion analyzer 610 continuously receives as input a plurality of images, $I_1, I_2, \ldots, I_n$, and produces as output a binary array, $B(i, j)$, of one's and zero's where one's indicate pixel locations $(i, j)$ at which motion has been detected.

As shown in FIG. 6, motion analyzer 610 includes three phases; namely, (i) an image integrator 620 that integrates a number, n, of live images 630 recorded by a video recorder, (ii) a frame comparator that compares pixel values between images, and (iii) a noise filter that removes noise captured in the video recorder. Operating conditions of motion analyzer 610 are such that the level of noise may be higher than the level of movement to be detected, especially in low light surroundings. Since motion analyzer 610 is required to detect subtle movement, a challenge of the system is to appropriately filter the noise so as to maximize motion detection intelligence.

Typically, pixel values are specified by a rectangular array of integer or floating point data for one or more color channels. Familiar color systems include RGB red-green-blue color channels, CMYK cyan-magenta-yellow-black color channels and YUV luminance-chrominance color channels. For the present analysis, noise for color channel data is modeled as being Gaussian additive; i.e., if $I(i, j)$ denotes the true color data at pixel location $(i, j)$ for a color channel, and if $G(i, j)$ denotes the color value measured by a video recorder, then $$G(i,j) = I(i,j) + \epsilon(i,j), \text{where } \epsilon(i,j) \sim N(\mu, \sigma^2), \quad (1)$$

with mean $\mu$, which is assumed to be zero, $\mu=0$, and variance $\sigma^2$. Preferably, the values $I(i, j)$ are luminance values.

Image integrator 620 receives as input a time series of n images, with pixel data denoted $G_1(i, j), G_2(i, j), \ldots, G_n(i, j)$, and produces as output an integrated image $I(i, j)$. Preferably, image integrator 620 reduces the noise level indicated in Equation (1) by averaging. Thus if $I(i, j)$ denotes the color data at pixel location $(i, j)$ after integrating the n images, then the noise level can be reduced by defining:

$$I(i, j) = \frac{1}{n} \sum_{k=1}^{n} G_k(i, j). \quad (2)$$

As each additional image $G_{n+1}(i, j)$ is integrated within image integrator 620, the averaged pixel values are accordingly incremented dynamically as follows:

$$I(i, j) \leftarrow I(i, j) + \frac{G_{n+1}(i, j) - G_1(i, j)}{n}. \quad (3)$$

For the present invention, an approximation to Equation (3) is used instead; namely, $$I(i, j) \leftarrow I(i, j) + \frac{G_{n+1}(i, j) - I(i, j)}{n}, \quad (4)$$

where $I(i, j)$ has been used instead of $G_1(i, j)$. The advantage of Equation (4) over Equation (3) is that use of Equation (4) does not require maintaining storage of the raw image data $G_1(i, j), G_2(i, j), \ldots, G_n(i, j)$ over a history of n images.

An advantage of averaging image data, as in Equation (2) above, is the elimination of noise. However, a disadvantage of averaging is that it tends to eliminate subtle movements, and especially periodic movement, making it hard to derive estimates of motion by comparing two images close in time. Thus in order to compensate for averaging, the present invention compares two images that are separated in time by approximately 1 second. In turn, this requires that a circular storage buffer of integrated images $I(i, j)$ is maintained over a corresponding time span of approximately 1 second. For a video recording frame rate of, say, 15 frames per second, this corresponds to a circular buffer of approximately 15 images.

Image comparator 640 receives as input the integrated images $I(i, j)$ generated by image integrator 620, and produces as output a rectangular array, $A(i, j)$, of binary values (one's and zero's) that correspond to pixel color value differences. Image comparator 640 determines which portions of the images are moving, and operates by comparing two integrated images that are approximately 1 second apart in time. Preferably, image comparator 640 uses differential changes instead of absolute changes, in order to avoid false movement detection when global lighting conditions change.

Denote by $IA(i, j)$ and $IB(i, j)$ two integrated images that are approximately one second apart in time, and that are being compared in order to extract motion information. Absolute differences such as $|IA(i,j) - IB(i,j)|$ are generally biased in the presence of a change in global lighting conditions. To avoid such a bias, image comparator 640 preferably uses differential changes of the form:

$$\Delta(i,j) = |IA(i,j) - IA(i - \delta_1, j - \delta_2)| - |IB(i,j) - IB(i - \delta_1, j - \delta_2)|. \quad (5)$$

Equation (5) incorporates both a spatial difference in a gradient direction ($\delta_1$, $\delta_2$), and a temporal difference over an approximate 1 second time frame. It is noted that a spatial difference generally eliminates global biases. Preferably, image comparator 640 uses a sum of several such terms (5) over several different gradient directions.

After computing the differences A(i, j) at each pixel location (i,j), image comparator 640 preferably uses a threshold value to replace A(i, j) with 1 for values of A greater than or equal to the threshold value, and to replace A(i, j) with 0 for value of A less than the threshold value. As such the output of image comparator is a binary array, B(i, j), with values B=0 or B=1 at each pixel location (i, j).

The output of image comparator 640 is passed to noise filter 650 for applying active noise filters. Noise filter 650 receives as input the binary array representing pixel color value differences produced by image comparator 640, and produces as output a corresponding noise-filtered binary array. Operation of noise filter 650 is based on the premises that (i) motion generally shows up in multiple consecutive image differences, and not just in a single image difference; and (ii) motion generally shows up in a cluster of pixels, and not just in a single isolated pixel. Accordingly, noise filter 650 modifies the binary array B(i,j) by zeroing out values B(i, j)=1 unless those values of one's have persisted throughout some number, m, of consecutive comparison arrays B over time; and (ii) erosion is applied to the thus modified array B(i, j) so as to zero out values of B(i,j)=1 at isolated pixels locations (i, j).

The binary array B(i, j) output by noise filter 650 corresponds to true motion; i.e., the pixel locations where B(i, j)=1 correspond to locations where true motion is detected.

State Detection

Figure 7:
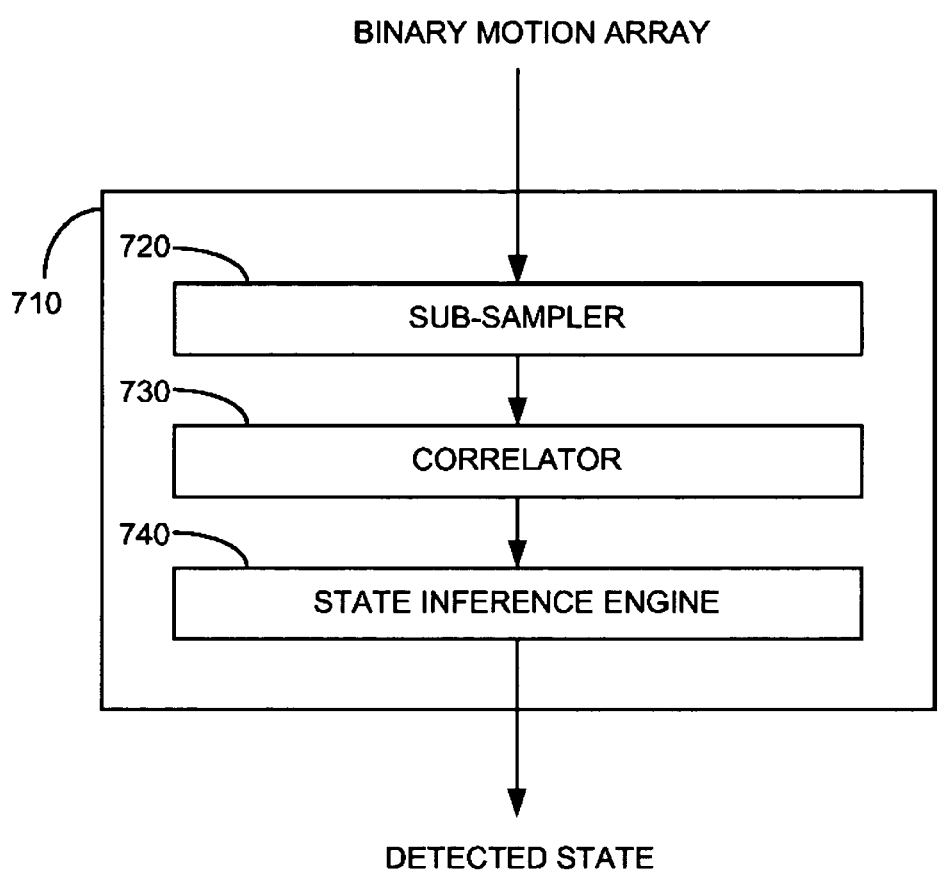
FIG. 7 is a simplified block diagram of a state detector, in accordance with a preferred embodiment of the present invention.

The operation of state detectors 140, 240 and 340 in FIGS. 1-3, respectively, and motion analysis steps 430 and 520 in FIGS. 4 and 5, respectively, will now be described in detail. Reference is now made to FIG. 7, which is a simplified block diagram of a state detector, in accordance with a preferred embodiment of the present invention. Shown FIG. 7 is a state detector 710 that receives as input a binary array, B(i, j), of one's and zero's indicating pixel locations where motion is detected. Such an array is normally output from motion detector 610. State detector 710 produces as output one or more automatically inferred states, that describe the subject being monitored.

State detector 710 performs three phases, as follows: (i) a sub-sampler 720 sub-samples the binary motion array to reduce it to a smaller resolution, (ii) a correlator 730 derives a measure of correlation between the current sub-sampled binary motion array and previous such arrays corresponding to times between 2 and 6 seconds prior to the current time, and (iii) a state inference engine 740 uses the measure of correlation to infer state information about the subject being monitored.

Based on the motion detection arrays B(i, j) output by the motion detection phase, pattern analysis is performed to detect if the motion exhibits repetitive patterns. Generally, a repetitive pattern indicates that the subject is sleeping, a non-repetitive pattern indicates that the subject is awake, and no motion for a period of 20 seconds indicates a state of alert.

Sub-sampler 720 accepts as input a binary array, B(i, j) of one's and zero's, and produces as output a binary array, BS(x, y), of smaller dimensions, that corresponds to a sub-sampled version of the input array, B(i, j). In accordance with a preferred embodiment of the present invention, sub-sampler 720 proceeds by sub-sampling the binary motion detection arrays B(i, j) to reduced resolution arrays, BS(x, y), of dimensions K×L pixels, wherein each sub-sampled pixel location (x, y) within BS corresponds to a rectangle R(x, y) of pixel locations (i, j) in a local neighborhood of the pixel location corresponding to (x, y) within B. Specifically, the sub-sampling operates by thresholding the numbers of pixel locations having B(i, j)=1 within each rectangle, so that BS(x, y) is assigned a value of 1 when the number of pixel locations (i, j) in rectangle R(x, y) satisfying B(i, j)=1 exceeds a threshold number.

Preferably, the sub-sampled binary arrays BS are stored in a circular queue that spans a timeframe of approximately 6 seconds.

Correlator 730 accepts as input the sub-sampled arrays BS(x, y) produced by sub-sampler 720, and produces as output measures of correlation, C, ranging between zero and one. Correlator 730 preferably derives a measure of correlation, C, at each time, T, as follows:

$$C = \max\left\{ \frac{M(t)}{M(t) + N(t)} : T - 6 \leq t \leq T - 2 \right\}, \text{ where} \qquad (6)$$

M(t) is the number of sub-sampled pixel locations (x, y) at which BS(x,y)=1 at the current time and BS(x, y)=1 at time t (a match), and N(t) is the number of sub-sampled pixel locations (x, y) at which B(x,y)=1 at the current time and BS(x, y)=0 at time t (a non-match). The restriction of t to being at least 2 seconds away from T is to ignore the high correlation between any two images that are recorded at almost the same time. It will be appreciated by those skilled in the art that the value of M(t) and N(t) can be efficiently computed by using conventional AND and NOT Boolean operations.

State detection engine 740 accepts as input the measures of correlation generated by correlator 730, and produces as output one or more inferred states. Based on the time series of the correlation measures, C, state detection engine 740 proceeds based on empirical rules.

As mentioned hereinabove, in accordance with a preferred embodiment of the present invention, repetitiveness is used to characterize a subject's sleep. If the subject is moving, which is manifested in a lack of repetitiveness, then he is more likely to be in a soft sleep; whereas if the subject does not move for a specific amount of time, which is manifested in a presence of repetitiveness, then he is more likely to be in a deep sleep. The correlation measures, C, are used as indicators of repetitive motion.

An example set of empirical rules that governs state determination is based on the premise that if C exceeds a threshold value, then the motion is repetitive, and was repeated at least 2 seconds before the current time. If C remains large for more than 60 seconds, then the person is sleeping. Otherwise, the person is awake. If no movement is detected for 20 seconds or longer, a state of alert is identified and preferably an alarm is sounded.

User Interface

Reference is now made to FIG. 8, which is an illustration of a user interface window 810 for real-time automated sleep monitoring, in accordance with a preferred embodiment of the present invention. The user interface of FIG. 8 is displayed on the video monitor of a PC computer, for a system of the present invention designed according to the architecture of FIG. 2. As described hereinabove in regards to FIG. 2, the present invention can be embodied using a standard baby monitor kit, which includes a video camera and a remote display unit. The remote display unit is connected to a PC computer that runs a special software application that performs steps 415-450 of FIG. 4.

Window 810 includes seven primary display areas, as follows. Display area 820 is a camera view, which displays in real-time the images that are currently being recorded. Display area 830 is an event information view, which displays a running history of states and events while the application is running. Display area 840 includes a moving time graph of the degree of motion detected, and a continuous text display of summary data. Display area 850 includes three LED-like displays that indicate whether the subject is sleeping, awake, or if no motion is detected. Display area 860 includes three button controls for (i) starting a sleep monitoring session, (ii) stopping the session, and (iii) configuring the software application. Display area 870 includes a fill-type indicator for lighting conditions, and indicates whether the lighting conditions where the subject is located are below normal for the application. Finally, display area 880 includes a control button to launch a viewer application that launches the user interface of FIG. 9.

It may thus be appreciated that the user interface of FIG. 8 provides real-time monitoring of a remote subject that includes image data and state information.

Reference is now made to FIG. 9, which is an illustration of a user interface window 910 for post-session review of images and state data collected during one of a plurality of sleep monitoring sessions, in accordance with a preferred embodiment of the present invention. As above with FIG. 8, the user interface of FIG. 9 is also displayed on the video monitor of a PC computer.

Window 910 includes five primary display areas, as follows. Display area 920 includes a list of stored monitoring sessions, sorted by date and time. Each new session that is monitored is stored and added to the list. When a user selects an entry in the list, image and state data from the selected session are displayed. Stored sessions can be purged by selecting one or more entries in the list and clicking on the wastebasket icon. Generally, a typical monitored 8-hour session requires approximately 25 MB of storage.

Display area 930 includes a graphic cylindrical shaped time-line summarizing states and events that occurred during the selected monitoring session. For ease of reference, the states are color-coded. As such, the color of a portion of the time-line indicates a state or event, and the length of the portion indicates its time duration. Display area 930 also includes a ruler directly above the time-line with times marked on it, so that the actual time corresponding to each portion of the time-line can be easily noted.

Reference is now made to FIGS. 10A and 10B, which are more detailed illustrations of a time-line display 930 of FIG. 9, in accordance with a preferred embodiment of the present invention. Preferably, identified states include inter alia (i) sleeping, (ii) awake, and (iii) no motion detected. Identified events include inter alia (i) 10 sec. apnea, (ii) low breath rhythm, (iii) moving while sleeping, and (iv) deep refresh sleep.

The time-line displays of FIGS. 10A and 10B enable one to determine the count of identified events during a session, or during an interval of time such as one hour. Normal sleep typically includes up to five periods of 10 sec. apnea per hour. Low breath rhythm preferably corresponds to less than 10 breaths per minute, which is very relevant when the person being monitored is an infant. The number of "moving while sleeping" periods indicates how fragmented the subject's sleep is. Refresh sleep preferably indicates a period of at least 5 min. of sleep without motion except for breathing. The percentage of total sleep that is comprised of refresh sleep is a measure of quality of sleep.

Referring back to FIG. 9, display area 940 includes scroll controls for navigating the time-lines of FIGS. 10A and 10B by scrolling to the right and to the left. Moreover, when a user clicks on an event in the time-line using a mouse, a video of that portion of the monitored session is automatically displayed.

Display area 950 includes a summary box with important statistics about the subject's sleep during the monitored session. Such statistics include inter alia (i) the start and stop time of the monitored session; (ii) total sleep time and periods of sleep, (iii) number of times the person moved during sleep, and (iv) duration and number of refresh sleep periods, and the percentage of total sleep time that was refresh sleep. Generally, a percentage of 0-10% indicates poor sleep, a percentage of 10-20% indicates normal sleep, a percentage of 20-30% indicates good quality sleep, and a percentage above 30% indicates very good quality sleep. Thus it may be appreciated that devices of the present invention can be used by individuals to monitor their own sleep, similar to the way devices are used to monitor pulse and other cardiac statistics.

Display area 960 includes a video screen for viewing the images recorded when specific events occurred. Thus when a user clicks on an event within the time-lines of FIGS. 10A and 10B, the images recorded during such event are automatically displayed in display area 960.

Reference is now made to FIG. 11, which is an illustration of a user interface window 1110 for monitoring infants, in accordance with a preferred embodiment of the present invention. The user interface window of FIG. 11 is also being displayed on a PC computer video monitor, where the PC is running special application software for performing the algorithms of the present invention. FIG. 11 is similar to FIG. 8, except that the user interface of FIG. 8 is customized for general sleep monitoring, and the user interface of FIG. 11 is customized for infant monitoring.

Window 1110 includes 8 primary display areas, as follows. Display area 1120 is a real-time display of images currently being recorded. Display area 1130 includes a running history of event information, describing events that have occurred during the current monitoring session. Display area 1140 includes a continuous time graph of movement during the current monitoring session, and a current text display of summary information. Display area 1150 includes three LED-like displays indicating whether the infant is (i) sleeping, (ii) awake or (iii) not moving. Display area 1160 includes three button controls for (i) starting a monitoring session, (ii) stopping a monitoring session, and (iii) configuring the software application.

Display area 1170 includes a fill-type indicator of lighting conditions, indicating whether lighting around the infant is below normal. Preferably, the present invention has a selection for day mode and night mode, where night mode is calibrated for dimly lit surroundings. If the application is running in day mode, and display area 1170 indicates below normal lighting conditions, then this indicates that the night mode should be used instead.

Figure 12:
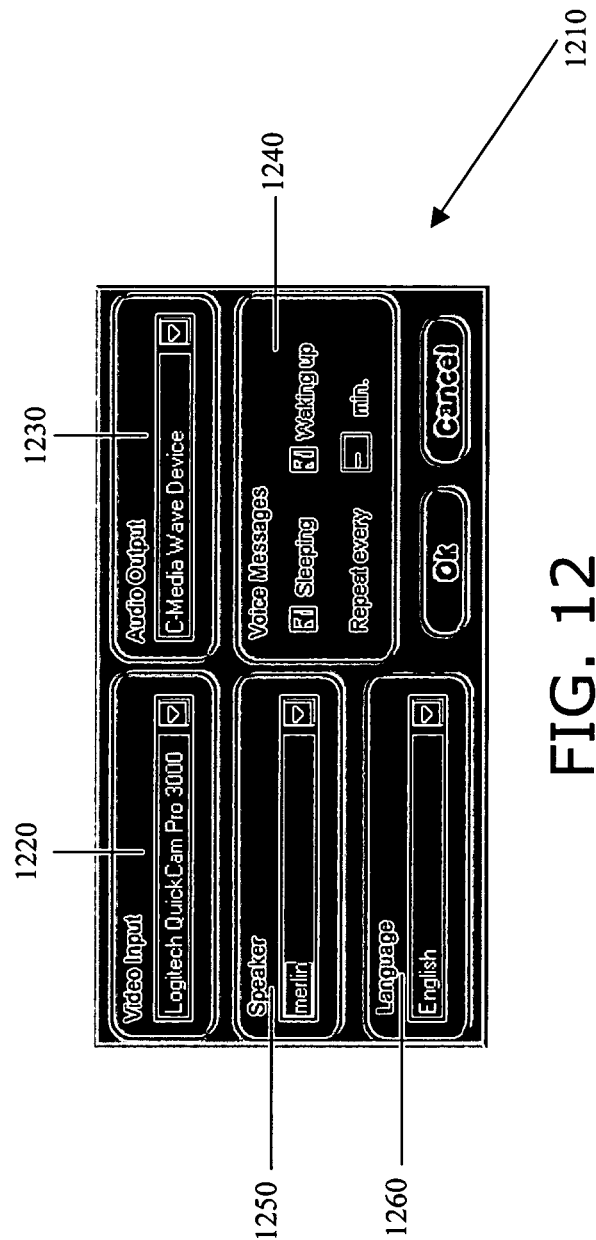
FIG. 12 is an illustration of a user interface window for configuring a software application that monitors infants, such as the software related to FIG. 11, in accordance with a preferred embodiment of the present invention.

Display area 1180 includes a selectable character, such as Merlin, which provides vocal information while the infant is being monitored. Preferably, the vocal information can be scheduled to play during fixed time intervals, such as every 10 minutes, as illustrated in FIG. 12. Display area 1190 shows the live images currently being recorded.

Reference is now made to FIG. 12, which is an illustration of a user interface window 1210 for configuring a software application that monitors infants, such as the software that uses the interface of FIG. 11, in accordance with a preferred embodiment of the present invention. Window 1210 includes five primary display areas. Display area 1220 is used for selecting a video input. Display area 1230 is used for selecting an audio sound card.

Display area 1240 is used for configuring voice messages; specifically, the messages vocalized by the character indicated as element 1180 of FIG. 11. Options include hearing messages when the infant transitions from a sleep state to an awake state, and when the infant transitions from an awake state to a sleep state. Options further include a "repeat every x minutes" setting, which enables a message about the current state of the infant to be sounded every time interval of x minutes, in addition to the change-of-state sleep and awake transitions.

Display area 1250 is used to set a character whose voice is used for messages. Display area 1260 is used to select a language for voice messages.

Additional Considerations

The ability of the present invention to automatically infer the state of a subject, leads naturally to a variety of auxiliary sleep-related functions that the present invention enables. In general, it will be appreciated that knowledge of the state of a subject being monitored in bed enables a system to perform services that are adapted to the subject's current state.

One such service is playback of pre-recorded sounds based on the subject's state. It is known that infants typically react favorably to certain sounds, such as lullabies or a parent's voice. A system embodying the present invention can be programmed to automatically play these sounds when the system detects that the infant wakes up at night.

Another such service is an intelligent alarm clock. It is known that being woken up while in a state of deep sleep is more violent on a subject's brain than being woken up while in a soft sleep. A system embodying the present invention can be programmed to play a wake-up alarm at a favorable moment within a specified time period, such as a moment within a 20-minute time interval during which a subject is not in a state of deep sleep, if such a moment occurs.

Having read the above disclosure, it will be appreciated by those skilled in the art that the present invention enables real-time automated mobile state monitoring of a remote site, and has widespread application to fields other than sleep monitoring. For example, the present invention has broad application to the fields of medical surveillance, security surveillance, military surveillance, geographical exploration and space exploration.

In reading the above description, persons skilled in the art will realize that there are many apparent variations that can be applied to the methods and systems described. Thus it may be appreciated that although FIGS. 1-5 indicate the use of wireless communication, other modes of communication may be used instead. For example, IP cameras that use digital networks, which may or may not be wireless, can be used for image capture. Similarly, the video recorder and display device illustrated in FIGS. 1-3 may be wired within a home. Wired communication may provide faster data transfer rates than wireless communication.

Similarly, although FIGS. 1-5 indicate the use of video recorders at the image capture side and display units at the monitoring side, other devices may be used instead at either side, such as mobile phones, personal data assistants (PDAs), and socket PC's such as those manufactured by Chip PC® Technologies of Haifa, Israel.

In the foregoing specification, the invention has been described with reference to specific exemplary embodiments thereof. It will, however, be evident that various modifications and changes may be made to the specific exemplary embodiments without departing from the broader spirit and scope of the invention as set forth in the appended claims. Accordingly, the specification and drawings are to be regarded in an illustrative rather than a restrictive sense.

What is claimed is:

1. Apparatus for automatically monitoring a subject's activity states, comprising:
   a video recorder for recording a time series of live images of a subject; and
   a computing device communicating with said video recorder that is programmed to:
      derive a time series of motion arrays wherein each element in each motion array corresponds to a location in a recorded live image at a given time, and indicates motion or absence of motion of the subject at the location at the given time;
      for each motion array in the time series and for each of a plurality of times T, calculate a metric of repetitive motion, designated as R(T), according to the equation, $$R(T) = \max\left\{ \frac{M(t)}{M(t) + N(t)} : T - \Delta 1 \leq t \leq T - \Delta 2 \right\}$$

wherein t is a time during a preceding time interval T−Δ1≦t≦T−Δ2 for which a motion array has been derived, wherein Δ1>Δ2, M(t) is the number of elements (x,y) at which an element (x,y) of the motion array at time T indicates motion and an element (x,y) of the motion array at time t also indicates motion, and N(t) is the number of elements (x,y) at which an element of the motion array at time T indicates motion and an element (x,y) of the motion array at time t indicates absence of motion; and
      automatically infer information about the activity states of the subject from the thus calculated metrics of repetitive motion.

2. The apparatus of claim 1 further comprising a monitor for displaying information inferred by said computing device about the activity states of the subject and for displaying the recorded live images.

3. The apparatus of claim 2 wherein said computing device further comprises a display control for activating said monitor whenever the information inferred about the state of the subject is deemed significant.

4. The apparatus of claim 1 wherein activity states of the subject include any of "sleeping", "awake", "no motion", "soft sleep", and "deep sleep".

5. The apparatus of claim 1 wherein said computing device further comprises a log manager for maintaining a log of movement-related information.

6. The apparatus of claim 1 wherein said computing device further comprises:
   a non-volatile memory; and
   a storage manager for selectively storing the recorded live images information inferred about the activity states of the subject in said non-volatile memory, for subsequent post-analysis.

7. The apparatus of claim 1 wherein said video recorder further comprises an infrared detector for enhancing images of objects within a dark surrounding.

8. The apparatus of claim 1 wherein the preceding time interval is approximately from two to six seconds prior to time T.

9. The apparatus of claim 1 wherein a state of deep sleep is inferred if the metric of repetitive motion remains above a threshold for a specified period of time.

10. A computer-processor based method for automated monitoring of a subject's activity states, comprising:
   recording, by a video recorder, a time series of live images of a subject;
   transmitting, by the video recorder, the time series of recorded live images in real-time to a computing device;
   receiving the time series of recorded live images in real-time at the computing device;
   deriving, by the computing device, a time series of motion arrays, wherein each element in each motion array corresponds to a location in a recorded live image at a given time, and indicates motion or absence of motion of the subject at the location at the given time;
   for each motion array in the time series and for each of a plurality of times T, calculating, by the computing device, a calculate a metric of repetitive motion, designated as R(T), according to the equation, $$R(T) = \max\left\{\frac{M(t)}{M(t)+N(t)} : T - \Delta 1 \le t \le T - \Delta 2\right\}$$

wherein t is a time during a preceding time interval T−Δ1≦t≦T−Δ2 for which a motion array has been derived, wherein Δ1>Δ2, M(t) is the number of elements (x,y) at which an element (x,y) of the motion array at time T indicates motion and an element (x,y) of the motion array at time t also indicates motion, and N(t) is the number of elements (x,y) at which an element of the motion array at time T indicates motion and an element (x,y) of the motion array at time t indicates absence of motion; and
   automatically inferring, by the computing device, information about the activity states of the subject from the thus calculated metrics of repetitive motion.

11. The method of claim 10 further comprising displaying the recorded live images on a monitor coupled with the computing device.

12. The method of claim 11 further comprising activating said displaying whenever the information inferred about the activity states of the subject is deemed significant.

13. The method of claim 10 wherein activity states of the subject include any of "sleeping", "awake", "no motion", "soft sleep", and "deep sleep".

14. The method of claim 10 further comprising maintaining a log of movement-related information.

15. The method of claim 10 further comprising selectively storing the recorded live images and the information inferred about the state of the subject in a memory, for subsequent post-analysis.

16. The method of claim 10 wherein the preceding time interval is approximately from two to six seconds prior to time T.

17. The method of claim 10 wherein a state of deep sleep is inferred if the metric of repetitive motion remains above a threshold for a specified period of time.

18. Apparatus for automatically monitoring a subject's activity states, comprising:
   a video recorder for recording a time series of live images of a subject, comprising:
      a processor that is programmed to:
         (i) derive a time series of motion arrays, wherein each element in each motion array corresponds to a location in a recorded live image at a given time, indicates motion or absence of motion of the subject at the location at the given time;
         (ii) for each motion array in the time series and for each of a plurality of times T, calculate a metric of repetitive motion, designated as R(T), according to the equation, $$R(T) = \max\left\{\frac{M(t)}{M(t)+N(t)} : T - \Delta 1 \le t \le T - \Delta 2\right\}$$

wherein t is a time during a preceding time interval T−Δ1≦t≦T−Δ2 for which a motion array has been derived, wherein Δ1>Δ2, M(t) is the number of elements (x,y) at which an element (x,y) of the motion array at time T indicates motion and an element (x,y) of the motion array at time t also indicates motion, and N(t) is the number of elements (x,y) at which an element of the motion array at time T indicates motion and an element (x,y) of the motion array at time t indicates absence of motion; and
         (iii) automatically infer information about the activity states of the subject from the thus calculated metrics of repetitive motion; and
      a transmitter for transmitting the information inferred by said processor about the activity states of the subject in real-time to a mobile device; and
   a display device communicating with said transmitter, comprising:
      a receiver for receiving the transmitted information inferred by said processor about the activity states of the subject; and
      a monitor for displaying in real-time the received information inferred by said processor about the activity states of the subject.

19. The apparatus of claim 18 wherein said transmitter also transmits the recorded live images to said display device receiver, and wherein said monitor also displays the recorded live images.

20. The apparatus of claim 18 wherein said display device further comprises a display control for activating said monitor whenever the information inferred about the activity states of the subject are deemed significant.

21. The apparatus of claim 18 wherein activity states of the subject include any of "sleeping", "awake", "no motion", "soft sleep", and "deep sleep".

22. The apparatus of claim 18 wherein said video recorder further comprises a log manager for maintaining a log of movement-related information.

23. The apparatus of claim 18 wherein said video recorder further comprises:
   a non-volatile memory; and
   a storage manager for selectively storing the recorded live images and the information inferred about the activity states of the subject in said non-volatile memory, for subsequent post-analysis.

24. The apparatus of claim 18 wherein said video recorder further comprises an infrared detector for enhancing images of objects within a dark surrounding.

25. The apparatus of claim 18 wherein the preceding time interval is approximately from two to six seconds prior to time T.

26. The apparatus of claim 18 wherein a state of deep sleep is inferred if the metric of repetitive motion remains above a threshold for a specified period of time.

27. A computer processor-based method for automated monitoring of a subject's states, comprising:

recording, by a video recorder, live images of a subject;
deriving, by the video recorder, a time series of motion arrays, wherein each element in each motion array corresponds to a location in a recorded live images at a given time, and indicates motion or absence of motion of the subject at the location at the given time;
calculating, by the video recorder, a metric of repetitive motion, designated as R(T), according to the equation, $$R(T) = \max\left\{\frac{M(t)}{M(t)+N(t)} : T - \Delta 1 \leq t \leq T - \Delta 2\right\}$$

wherein t is a time during a preceding time interval T−Δ1≦t≦T−Δ2 for which a motion array has been derived, wherein Δ1>Δ2, M(t) is the number of elements (x,y) at which an element (x,y) of the motion array at time T indicates motion and an element (x,y) of the motion array at time t also indicates motion, and N(t) is the number of elements (x,y) at which an element of the motion array at time T indicates motion and an element (x,y) of the motion array at time t indicates absence of motion;
automatically inferring, by the video recorder, information about the activity states of the subject from the thus calculated metrics of repetitive motion;
transmitting, by the video recorder, the information inferred about the activity states of the subject to a display device;
receiving the information inferred about the activity states of the subject at the display device; and
displaying the information inferred about the activity states of the subject on the display device.

28. The method of claim 27 wherein said transmitting also transmits the recorded live images to the display device, wherein said receiving also receives the recorded live images, and wherein said displaying also displays the recorded live images.

29. The method of claim 27 further comprising activating said displaying whenever the information inferred about the activity states of the subject is deemed significant.

30. The method of claim 27 wherein activity states of the subject include any of "sleeping", "awake", "no motion", "soft sleep", and "deep sleep".

31. The method of claim 27 further comprising maintaining a log of movement-related information.

32. The method of claim 27 further comprising selectively storing the recorded live images and the information inferred about the activity states of the subject in a memory, for subsequent post-analysis.

33. The method of claim 27 wherein the preceding time interval is approximately from two to six seconds prior to time T.

34. The method of claim 27 wherein a state of deep sleep is inferred if the metric of repetitive motion remains above the threshold for a specified period of time.

35. A computing device for automatically monitoring a subject's activity states, comprising:
a receiver for receiving time series of live images of a subject from a live video recorder; and
a processor that is programmed to:
derive a time series of motion arrays, wherein each element in each motion array corresponds to a location in a recorded live image at a given time, and indicates motion or absence of motion of the subject at the location at the given time;
for each motion array in the time series and for each of a plurality of times T, calculate a metric of repetitive motion, designated as R(T), according to the equation, $$R(T) = \max\left\{\frac{M(t)}{M(t)+N(t)} : T - \Delta 1 \leq t \leq T - \Delta 2\right\}$$

wherein t is a time during a preceding time interval T−Δ1≦t≦T−Δ2 for which a motion array has been derived, wherein Δ1>Δ2, M(t) is the number of elements (x,y) at which an element (x,y) of the motion array at time T indicates motion and an element (x,y) of the motion array at time t also indicates motion, and N(t) is the number of elements (x,y) at which an element of the motion array at time T indicates motion and an element (x,y) of the motion array at time t indicates absence of motion; and
automatically infer information about the activity states of the subject from the thus calculated metrics of repetitive motion.

36. The computing device of claim 35 further comprising a monitor for displaying information inferred by the computing device about the activity states of the subject and for displaying the recorded live images.

37. The computing device of claim 35 further comprising a display control for activating said monitor whenever the information inferred about the activity states of the subject are deemed significant.

38. The computing device of claim 35 wherein activity states of the subject include any of "sleeping", "awake", "no motion", "soft sleep", and "deep sleep".

39. The computing device of claim 35 further comprising a log manager for maintaining a log of movement-related information.

40. The computing device of claim 35 further comprising:
a non-volatile memory; and
a storage manager for selectively storing the recorded live images and the information inferred about the activity states of the subject in said non-volatile memory, for subsequent post-analysis.

41. A computer-implemented method for automated monitoring of a subject's activity states, comprising:
receiving, by a computing device, a time series of live images of a subject from a video recorder;
deriving, by the computing device, a time series of motion arrays, wherein each element in each motion array corresponds to a location in a received images at a given time, and indicates motion or absence of motion of the subject at the location at the given time;
for each motion array in the time series and for each of a plurality of times T, calculating, by the computing device, a metric of repetitive motion, designated as R(T), according to the equation, $$R(T) = \max\left\{\frac{M(t)}{M(t)+N(t)} : T - \Delta 1 \leq t \leq T - \Delta 2\right\}$$

wherein t is a time during a preceding time interval T−Δ1≦t≦T−Δ2 for which a motion array has been derived, wherein Δ1>Δ2, M(t) is the number of elements (x,y) at which an element (x,y) of the motion array at time T indicates motion and an element (x,y) of the motion array at time t also indicates motion, and N(t) is the number of elements (x,y) at which an element of the motion array at time T indicates motion and an element (x,y) of the motion array at time t indicates absence of motion; and automatically inferring, by the computing device, information about the activity states of the subject from the thus calculated metrics of repetitive motion.

42. The method of claim 41 further comprising displaying the information inferred about the activity states of the subject and the time series of live images on a monitor.

43. The method of claim 42 further comprising activating said displaying whenever the information inferred about the activity states of the subject are deemed significant.

44. The method of claim 41 wherein activity states of the subject include any of "sleeping", "awake", "no motion", "soft sleep", and "deep sleep".

45. The method of claim 41 further comprising maintaining a log of movement-related information.

46. The method of claim 41 further comprising selectively storing the received live images and the information inferred about the activity states of the subject in a memory, for subsequent post-analysis.

47. An enhanced video recorder for automatically monitoring a subject's activity states, comprising:

a memory for storing a time series of captured digital images of a subject;

a processor that is programmed to:

derive a time series of motion arrays, wherein each element in each motion array corresponds to a location in a captured digital image at a given time, and indicates motion or absence of motion of the subject at the location at the given time;

for each motion array in the time series and for each of a plurality of times T, calculate a metric of repetitive motion, designated as R(T), according to the equation, $$R(T) = \max\left\{\frac{M(t)}{M(t) + N(t)} : T - \Delta 1 \le t \le T - \Delta 2\right\}$$

wherein t is a time during a preceding time interval $T-\Delta 1 \le t \le T-\Delta 2$ for which a motion array has been derived, wherein $\Delta 1 > \Delta 2$, M(t) is the number of elements (x,y) at which an element (x,y) of the motion array at time T indicates motion and an element (x,y) of the motion array at time t also indicates motion, and N(t) is the number of elements (x,y) at which an element of the motion array at time T indicates motion and an element (x,y) of the motion array at time t indicates absence of motion; and automatically infer information about the activity states of the subject from the thus calculated metrics of repetitive motion; and a transmitter for transmitting the information inferred by said processor about the activity states of the subject to a display device.

48. The enhanced video recorder of claim 47 wherein said transmitter also transmits the captured digital images to the display device.

49. The enhanced video recorder of claim 47 wherein activity states of the subject include any of "sleeping", "awake", "no motion", "soft sleep", and "deep sleep".

50. The enhanced video recorder of claim 47 further comprising a log manager for maintaining a movement-related information.

51. The enhanced video recorder of claim 47 further comprising:

a non-volatile memory; and a storage manager for selectively storing the captured digital images and the information inferred about the activity states of the subject in said non-volatile memory, for subsequent post-analysis.

52. The enhanced video recorder of claim 47 further comprising an infrared detector for enhancing images of objects within a dark surrounding.

53. A computer-processor based method for automated monitoring of a subject's activity states by an enhanced video recorder, comprising:

recording, by the enhanced video recorder, a time series of live images of a subject;

deriving, by the enhanced video recorder, a time series of motion arrays, wherein each element in each motion array corresponds to a location in a recorded live image at a given time, and indicates motion or absence of motion of the subject at the location at a the given time;

for each motion array in the time series and for each of a plurality of times T, calculating, by the enhanced video recorder, a metric of repetitive motion, designated as R(T), according to the equation, $$R(T) = \max\left\{\frac{M(t)}{M(t) + N(t)} : T - \Delta 1 \le t \le T - \Delta 2\right\}$$

wherein t is a time during a preceding time interval $T-\Delta 1 \le t \le T-\Delta 2$ for which a motion array has been derived, wherein $\Delta 1 > \Delta 2$, M(t) is the number of elements (x,y) at which an element (x,y) of the motion array at time T indicates motion and an element (x,y) of the motion array at time t also indicates motion, and N(t) is the number of elements (x,y) at which an element of the motion array at time T indicates motion and an element (x,y) of the motion array at time t indicates absence of motion;

automatically inferring, by the enhanced video recorder, information about the activity states of the subject from the thus calculated metrics of repetitive motion; and transmitting the information inferred about the activity states of the subject to a display device in real-time.

54. The method of claim 53 wherein said transmitting also transmits in real-time the time series of recorded images to the display device.

55. The method of claim 53 wherein activity states of the subject include any of "sleeping", "awake", "no motion", "soft sleep", and "deep sleep".

56. The method of claim 53 further comprising maintaining a log of movement-related information.

57. The method of claim 53 further comprising selectively storing the recorded images and the information inferred about the activity states of the subject in a memory, for subsequent post-analysis.

58. A non-transitory computer-readable storage medium storing program code for causing a computing device to:

receive a time series of transmitted live images of a subject;

derive a time series of motion arrays, wherein each element in each motion array corresponds to a location in a received image at a given time, and indicates motion or absence of motion of the subject at the location at the given time;

for each motion array in the time series and for each of a plurality of times T, calculate a metric of repetitive motion, designated as R(T), according to the equation, $$R(T) = \max\left\{\frac{M(t)}{M(t)+N(t)} : T - \Delta 1 \leq t \leq T - \Delta 2\right\}$$

wherein t is a time during a preceding time interval T−Δ1≦t≦T−Δ2 for which a motion array has been derived, wherein Δ1>Δ2, M(t) is the number of elements (x,y) at which an element (x,y) of the motion array at time T indicates motion and an element (x,y) of the motion array at time t also indicates motion, and N(t) is the number of elements (x,y) at which an element of the motion array at time T indicates motion and an element (x,y) of the motion array at time t indicates absence of motion;
  automatically infer information about the activity states of the subject from the thus calculated metrics of repetitive motion; and
  display the information inferred about the activity states of the subject on a monitor coupled with the computing device.

59. A non-transitory computer-readable storage medium storing program code for causing an enhanced video recorder to:
  record a time series of live images of a subject;
  derive a time series of motion arrays, wherein each element in each motion array corresponds to a location in a recorded live image at a given time, and indicates motion or absence of motion of the subject at the location at the given time;
  for each motion array in the time series and for each of a plurality of times T, calculate a metric of repetitive motion, designated as R(T), according to the equation, $$R(T) = \max\left\{\frac{M(t)}{M(t)+N(t)} : T - \Delta 1 \leq t \leq T - \Delta 2\right\}$$

wherein t is a time during a preceding time interval T−Δ1≦t≦T−Δ2 for which a motion array has been derived, wherein Δ1>Δ2, M(t) is the number of elements (x,y) at which an element (x,y) of the motion array at time T indicates motion and an element (x,y) of the motion array at time t also indicates motion, and N(t) is the number of elements (x,y) at which an element of the motion array at time T indicates motion and an element (x,y) of the motion array at time t indicates absence of motion;
  automatically infer information about the activity states of the subject from the thus calculated metrics of repetitive motion; and
  transmit the information inferred about the activity states of the subject to a display device.

\* \* \* \* \*